United States Patent [19]

Kuwada et al.

[11] 3,978,058
[45] Aug. 31, 1976

[54] PYRIMIDO[1,2-a][1,5]BENZODIAZOCINE DERIVATIVES

[75] Inventors: Yutaka Kuwada; Hideaki Natsugari; Kanji Meguro, all of Hyogo, Japan

[73] Assignee: Takeda Chemical Industries, Ltd., Osaka, Japan

[22] Filed: Dec. 15, 1972

[21] Appl. No.: 315,313

[30] Foreign Application Priority Data
Dec. 24, 1971 Japan.................................. 46-2722
Nov. 18, 1972 Japan.............................. 47-115761

[52] U.S. Cl.................. 260/256.4 F; 260/239 BD; 424/251
[51] Int. Cl.².......................................... C07D 487/04
[58] Field of Search............................... 260/256.4 F

[56] References Cited
UNITED STATES PATENTS

| | | | |
|---|---|---|---|
| 3,651,046 | 3/1972 | Derieg et al.................. | 260/256.4 F |
| 3,734,912 | 5/1973 | Hanze........................... | 260/256.4 F |
| 3,755,300 | 8/1973 | Tachikawa et al. .......... | 260/256.4 F |
| 3,796,713 | 3/1974 | Derieg et al.................. | 260/256.4 F |

*Primary Examiner*—Alton D. Rollins
*Assistant Examiner*—James H. Turnipseed
*Attorney, Agent, or Firm*—Wenderoth, Lind & Ponack

[57] ABSTRACT

Novel compounds of the formula,

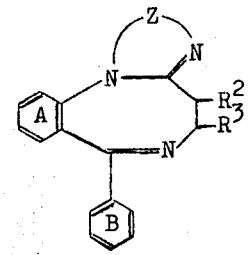

wherein

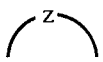

stands for the partial structure

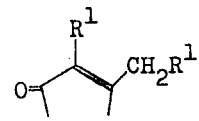

wherein R¹ stands for hydrogen atom, an alkyl group or phenyl group, R² and R³ stand for, the same or different, hydrogen atom or a lower alkyl group and rings A and B are unsubstituted or substituted by one or more, he same or different, of halogen atom, nitro, trifluoromethyl, a lower alkyl group or a lower alkoxy group, have sedative, anti-inflammatory, anti-convulsive, sleep-potentiating and diuretic activites.

15 Claims, 4 Drawing Figures

PYRIMIDO[1,2-a][1,5]BENZODIAZOCINE DERIVATIVES

This invention relates to novel and useful benzodiazocine derivatives having sedative, anti-inflammatory, anti-convulsive, sleep-potentiating and diuretic activites.

More specifically, the present invention relates to pyrimidobenzodiazocine derivatives of the formula (I);

wherein stands for the partial structure wherein $R^1$ stands for hydrogen atom, an alkyl group or a phenyl group, $R^2$ and $R^3$ stand for, the same or different, hydrogen atom or a lower alkyl group and rings A and B are unsubstituted or substituted by one or more, the same or different, of halogen atom, nitro, trifluoromethyl, a lower alkyl group or a lower alkoxy group, and its pharmaceutically acceptable acid addition salts and relates to the production thereof. In the formula (I), the alkyl group designated by $R^1$ has preferably 1 to 6 carbon atoms, and more preferably 1 to 3 carbon atoms, and are exemplified by methyl, ethyl, propoyl, isopropyl, butyl, isobutyl, secbutyl, tert-butyl, pentyl, cyclopentyl, 2-methylbutyl, neopentyl, hexyl, cyclohexyl, 2-methylpentyl, 3-methylpentyl.

The lower alkyl groups designated by $R^2$ and $R^3$ have preferably 1 to 3 carbon atoms, and are exemplified by methyl, ethyl, propyl.

Rings A and B have no substituent or have one or more, the same or different, substituent(s) at any position(s). The halogen atoms which may be substituted on rings A and B are exemplified by chlorine, fluorine, bromine, iodine. The lower alkyl groups which may be substituted on rings A and B have preferably 1 to 4 carbon atoms and are exemplified by methyl, ethyl, propyl, isopropyl, butyl. The alkoxy groups which may be substituted on rings A and B have preferably 1 to 4 carbon atoms and are exemplified by methoxy, ethoxy, propoxy, isopropoxy, butoxy.

The compound (I) is represented by either of the following formulas:

wherein $R^1$, $R^2$ and $R^3$ and rings A and B are the same meaning as defined above.

The compound (I) is produced by subjecting a compound of the formula (II);

wherein $R^1$, $R^2$ and $R^3$ and rings A and B have the same meaning as defined above and the group —COCH($R^1$-

)COCH$_2$R$^1$ may be attached to either the nitrogen at 1-position or the nitrogen of amino group at 2-position, to cyclodehydration reaction. The compound (II) is also represented by either of the following formulas;

(II-A)

(II-B)

wherein R$^1$, R$^2$ and R$^3$ and rings A and B are the same meaning as defined above.

The cyclodehydration reaction is in general conducted with heating or in the presence of a dehydrating agent.

In case the reaction is conducted with heating, it proceeds without solvent or with a conventional solvent. The solvent may be conventional one such as aromatic hydrocarbons (e.g. benzene, toluene, xylene and chlorobenzene), halogenated aliphatic hydrocarbons (e.g. chloroform and dichloroethane), ketones (e.g. methyl ethyl ketone) and ethers (e.g. dioxane and tetrahydrofuran). The reaction with heating is conducted at a temperature ranging from 50° to 200°C, more preferably from 70° to 150°C.

In case a dehydrating agent is employed, the reaction is advantageously conducted in the presence of a conventional solvent such as alcohols (e.g. methanol, ethanol and propanol), halogenated aliphatic hydrocarbons (e.g. chloroform and methylene chloride) and aromatic hydrocarbons (e.g. benzene, toluene and xylene) at a temperature ranging from −50° to 50°C, and preferably from −10° to 30°C. As a dehydrating agent, an acid or a chloride or an oxychloride of sulfur or phosphor is employed. The acid is exemplified by inorganic acids (e.g. hydrogen chloride, hydrogen bromide, sulfuric acid and polyphosphoric acid), organic carboxylic acids (e.g. acetic acid, propionic acid and trifluoroacetic acid) and organic sulfonic acids (e.g. methane sulfonic acid, benzenesulfonic acid and toluene sulfonic acid), and, above all, hydrogen chloride is preferably employed. The chloride or oxychloride is exemplified by thionyl chloride, phosphorus oxychloride, phosphorus trichloride and phosphorus pentachloride. The said dehydrating agent is employed from 1 to 20 moles, preferably 2 to 10 moles per mole of the compound (II). When a large excess of the dehydrating agent is employed, it can act also as a solvent. When an acid is used as the dehydrating agent in the reaction the compound (I) is obtained in the form of an acid addition salt. The acid addition salt may easily be converted to the free base by means of per se conventional neutralizing agent (e.g. ammonia, alkali hydroxides, alkali carbonates and alkali bicarbonates).

By the cyclodehydration under heating, the compound (II) changes into the compound (I-B) through intra-molecular cyclization. And, by the cyclodehydration reaction of the compounds (II-A) and (II-B) in the presence of a dehydrating agent, the respective compounds (I-A) and (I-B) are produced through intramolecular cyclization.

And a mixture of the compound (II-A) and (II-B) can be used as it is for the preparation of (I-B) by the cyclodehydration reaction with heating. The mixture of the compound (II-A) and (II-B), of course, may be used in cyclodehydration reaction in the presence of a dehydrating agent. In the latter case the product (I) is obtained as a mixture of the compound (I-A) and (I-B) and they can easily be separated and purified by per se conventional means (e.g. recrystallization and chromatography).

The compound (II) can be prepared by reacting a compound (III) represented by the formula;

(III)

wherein R$^2$ and R$^3$ and rings A and B have the same meaning as defined above, with diketene or its derivative (IV) represented by the formula (IV)

wherein R$^1$ has the same meaning as defined above.

The amount of the compound (IV) is generally 1 to 20 moles, preferably 1 to 5 moles and more preferably 2 to 5 moles per mole of the compound (III). This reaction may be conducted in the absence or presence of an inert solvent such as aromatic hydrocarbons (e.g. benzene, toluene and xylene), aliphatic halogenated hydrocarbons (e.g. chloroform, carbon tetrachloride and methylene chloride), ethers (e.g. tetrahydrofuran, dioxane and ethyl ether) and esters (e.g. ethyl acetate). The compound (IV) may be employed in a large excess as a solvent. The reaction is generally conducted at −50° to 200°C, preferably −10° to 100°C.

In this reaction, the compound (IV) reacts with either the nitrogen at 1-position of the nitrogen of the amino group at 2-position to give a mixture of the compound (II-B), i.e. 1-(acylacetyl) compound, and the compound (II-A), i.e. 2-(acylacetamido) compound.

The thus obtained mixture of compound (II-A) and (II-B) may be employed in the next reaction step as such or after separation from each other, as mentioned above. The said separation is easily conducted by recrystallization or column chromatography. Each of the products may be purified by a conventional purification method, for example recrystallization. When merely the compound (I-B) is desired, a mixture of the compound (III) and the compound (IV) is heated at a relatively higher temperature until the desired product is formed.

The thus obtained compound (II) is novel and useful not only as an intermediate for producing benzodiazocine derivatives such as the present compound (I), but also as medicines.

The compound (I) can form acid addition salts with suitable acids, and they may be prepared by a per se conventional process, if the compound (I) is collected in its free base. The acids are exemplified by inorganic acids (e.g. hydrochloric acid, hydrobromic acid and sulfuric acid), and organic acids (e.g. acetic acid, oxalic acid, malonic acid, succinic acid, malic acid, maleic acid, tartaric acid, benzenesulfonic acid and toluenesulfonic acid).

The compound (I), its acid addition salts and the compound (II) have effective sedative anti-inflammatory, anti-convulsive, sleep-potentiating and diuretic activities. Therefore they are useful as medicines such as sedatives, anti-inflammatory agent, anti-convulsives, sleep-potentiating agents and diuretics. They can be administered as it is or in admixture with a pharmaceutically acceptable carriers, either orally or parenterally in various forms such as powder, granule, tablet, capsule, liquid and injection. While the dosage varies with the types of the compounds, symptoms and with other factors, and usual daily dosage ranges from 10 mg. to 500 mg. for a human adult.

For further detailed explanation of the invention the following examples are given, wherein the term "parts(s)" means "weight part(s)" unless otherwise noted and the relationship between "part(s)" and "part(s) by volume" corresponds to that between "gram(s)" and "milliliter(s)".

EXAMPLE 1

Figure 1:
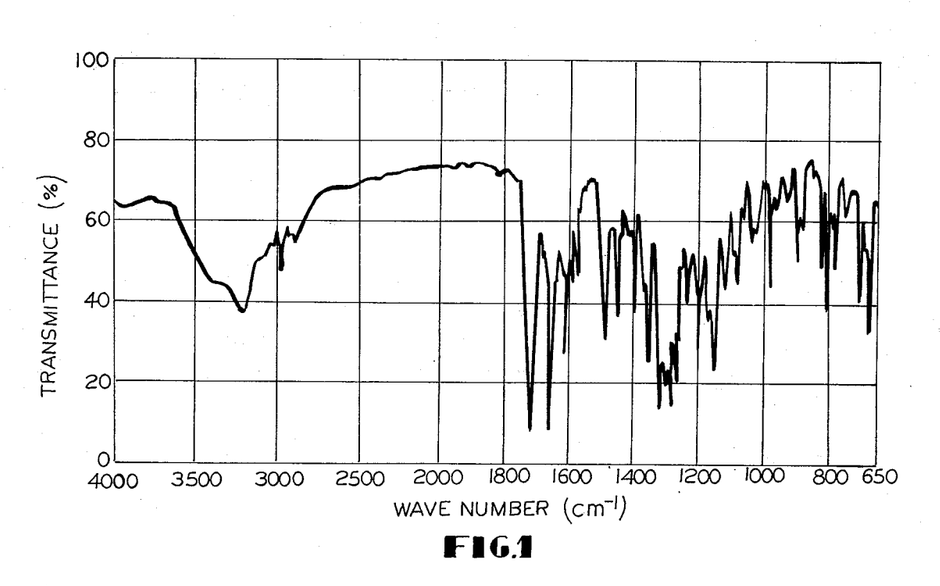

To a suspension of 5.0 parts of 2-amino-8-chloro-3,4-dihydro-6-phenyl-1,5-benzodiazocine in 100 parts by volume of benzene is added 3.0 parts by volume of diketene at 25°C with stirring. The reaction mixture is further stirred for 1.5 hour. Resulting colorless crystals are collected by filtration, washed with ether, whereby 1-acetoacetyl-8-chloro-2-imino-6-phenyl-1,2,3,4-tetrahydro-1,5-benzodiazocine is obtained. Melting point 149°–150°C.

Elementary analysis: $C_{20}H_{18}ClN_3O_2$. Calculated: C 65.30, H 4.93, N 11.42. Found: C 65.41, H 4.92, N 11.46.

The infrared absorption spectrum of the product is shown in FIG. 1.

Figure 2:
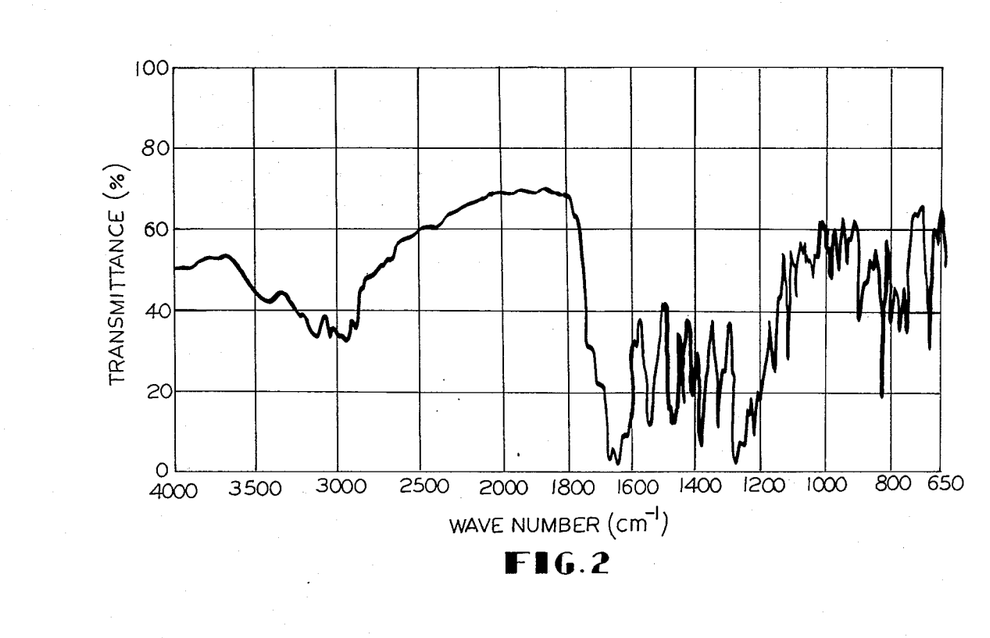

The filtrate is concentrated to dryness under reduced pressure. The residue is purified by chromatography on silica gel with acetone-n-hexane (3:2) to give 2-acetoacetamido-8-chloro-3,4-dihydro-6-phenyl-1,5-benzodiazocine as colorless crystals. Melting point 158°–159°C.

Elementary analysis: $C_{20}H_{18}ClN_3O_2$. Calculated: C 65.30, H 4.93, N 11.42. Found: C 64.96, H 4.81, N 11.32.

The infrared absorption spectrum of the product is shown in FIG. 2.

The following compounds are prepared in a similar manner to that in Example 1.

| Starting materials | Product | Melting point (°C) |
|---|---|---|
| 2-amino-3,4-dihydro-6-phenyl-1,5-benzodiazocine | 1-acetoacetyl-2-imino-6-phenyl-1,2,3,4-tetrahydro-1,5-benzodiazocine | 130–132 |
| + diketene | 2-acetoacetamido-3,4-dihydro-6-phenyl-1,5-benzodiazocine | 104–105 |
| 2-amino-3,4-dihydro-8-methyl-6-phenyl-1,5-benzodiazocine | 1-acetoacetyl-2-imino-8-methyl-6-phenyl-1,2,3,4-tetrahydro-1,5-benzodiazocine | 155–156 |
| + diketene | 2-acetoacetamido-3,4-dihydro-8-methyl-6-phenyl-1,5-benzodiazocine | 149–150 |
| 2-amino-3,4-dihydro-8,9-dimethoxy-6-phenyl-1,5-benzodiazocine | 1-acetoacetyl-8,9-dimethoxy-2-imino-6-phenyl-1,2,3,4-tetrahydro-1,5-benzodiazocine | 160–162 |
| + diketene | 2-acetoacetamido-3,4-dihydro-8,9-dimethoxy-6-phenyl-1,5-benzodiazocine | oily product |
| 2-amino-8-chloro-3,4-dihydro-4-methyl-6-phenyl-1,5-benzodiazocine | 1-acetoacetyl-8-chloro-2-imino-4-methyl-6-phenyl-1,2,3,4-tetrahydro-1,5-benzodiazocine | 155–157 |
| + diketene | 2-acetoacetamido-8-chloro-3,4-dihydro-4-methyl-6-phenyl-1,5-benzodiazocine | oily product |
| 2-amino-8-chloro-6-(4-chlorophenyl)-3,4-dihydro-3-methyl-benzodiazocine | 1-acetoacetyl-8-chloro-6-(4-chlorophenyl)-2-imino-3-methyl-1,2,3,4-tetrahydro-1,5-benzodiazocine | 142–144 |
| + diketene | 2-acetoacetamido-8-chloro-6-(4-chlorophenyl)-3,4-dihydro-3-methyl-1,5-benzodiazocine | 152–154 |

EXAMPLE 2

Figure 4:
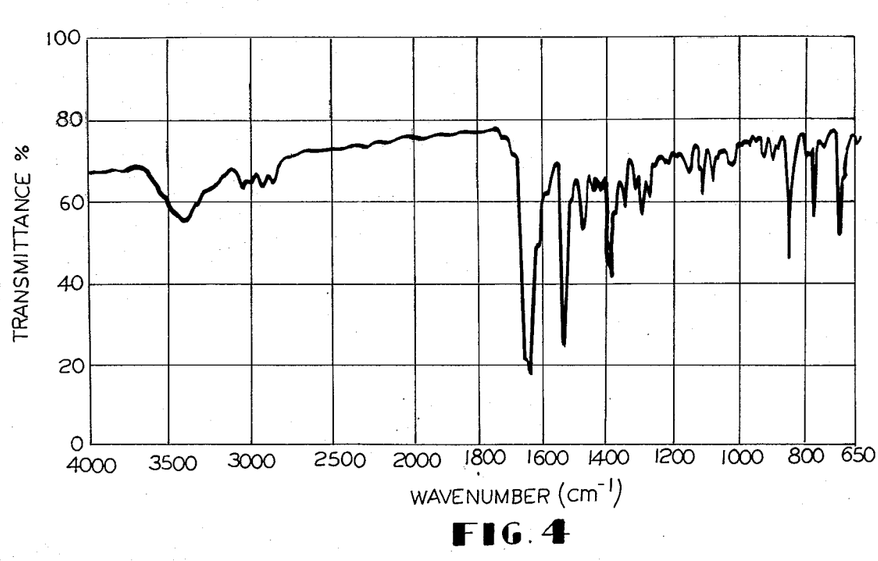

To a solution of 0.37 part of 2-acetoacetamido-8-chloro-3,4-dihydro-6-phenyl-1,5-benzodiazocine in 10 parts by volume of methanol is added 0.5 part by volume of methanol saturated with hydrogen chloride under stirring and ice cooling. The reaction mixture is further stirred for 25 minutes at 5°C, poured into aqueous ammonia and extracted with chloroform. The chloroform layer is washed with water, dried over sodium sulfate, then the solvent is removed under reduced pressure. The residue is treated with ether-n-hexane to give 10-chloro-5,6-dihydro-1-methyl-8-phenyl-3H-pyrimido(1,2-a)(1,5)benzodiazocin-3-one as colorless crystals. Recrystallization from dichloromethane-benzene gives colorless needles. Melting point 263°–265°C (decomp.).

Elementary analysis: $C_{20}H_{16}ClN_3O$. Calculated: C 68.67, H 4.61, N 12.01. Found: C 68.39, H 4.65, N 11.59.

The infrared absorption spectrum of the product is shown in FIG. 4.

The following compounds are prepared in a similar manner to that in Example 2.

| Starting material | Product | Melting point (°C) |
|---|---|---|
| 2-acetoacetamido-3,4- | 5,6-dihydro-1-methyl-8- | |

-continued

| Starting material | Product | Melting point (°C) |
|---|---|---|
| dihydro-6-phenyl-1,5-benzodiazocine | phenyl-3H-pyrimido(1,2-a)-(1,5)benzodiazocin-3-one | 265–267 |
| 2-acetoacetamido-3,4-dihydro-8-methyl-6-phenyl-1,5-benzodiazocine | 5,6-dihydro-1,10-dimethyl-8-phenyl-3H-pyrimido-(1,2-a)(1,5)benzodiazocin-3-one | 239–240 |
| 2-acetoacetamido-3,4-dihydro-8,9-dimethoxy-6-phenyl-1,5-benzodiazocine | 5,6-dihydro-10,11-dimethoxy-1-methyl-8-phenyl-3H-pyrimino(1,2-a)-(1,5)benzodiazocin-3-one | 259–260 |
| 2-acetoacetamido-8-chloro-3,4-dihydro-4-methyl-6-phenyl-1,5-benzodiazocine | 10-chloro-5,6-dihydro-1,6-dimethyl-8-phenyl-3H-pyrimido(1,2-a)(1,5)-benzodiazocin-3-one | 271–273 |
| 2-acetoacetamido-8-chloro-6-(4-chlorophenyl)-3,4-dihydro-3-methyl-1,5-benzodiazocine | 10-chloro-8-(4-chlorophenyl)-5,6-dihydro-1,5-dimethyl-3H-pyrimido-(1,2-a)(1,5)benzodiazocin-3-one | 274–275 |

EXAMPLE 3

To a solution of 0.25 part of 1-acetoacetyl-8-chloro-6-(4-chlorophenyl)-2-imino-3-methyl-1,2,3,4-tetrahydro-1,5-benzodiazocine in 15 parts by volume of chloroform is added 0.3 part by volume of thionyl chloride. The reaction mixture is heated at 50°C for 1 hour, cooled and poured into saturated sodium bicarbonate solution. The chloroform layer is separated, washed with water and dried over sodium sulfate, then the solvent is evaporated under reduced pressure. The residue is chromatographed on silica gel with chloroform to give 10-chloro-8-(4-chlorophenyl)-5,6-dihydro-3,5-dimethyl1H-pyrimido(1,2-a) 1,5)benzodiazocin-1-one as colorless crystals. Recrystallization from acetone-n-hexane gives colorless prisms. Melting point 214°–215°C.

EXAMPLE 4

Figure 3:
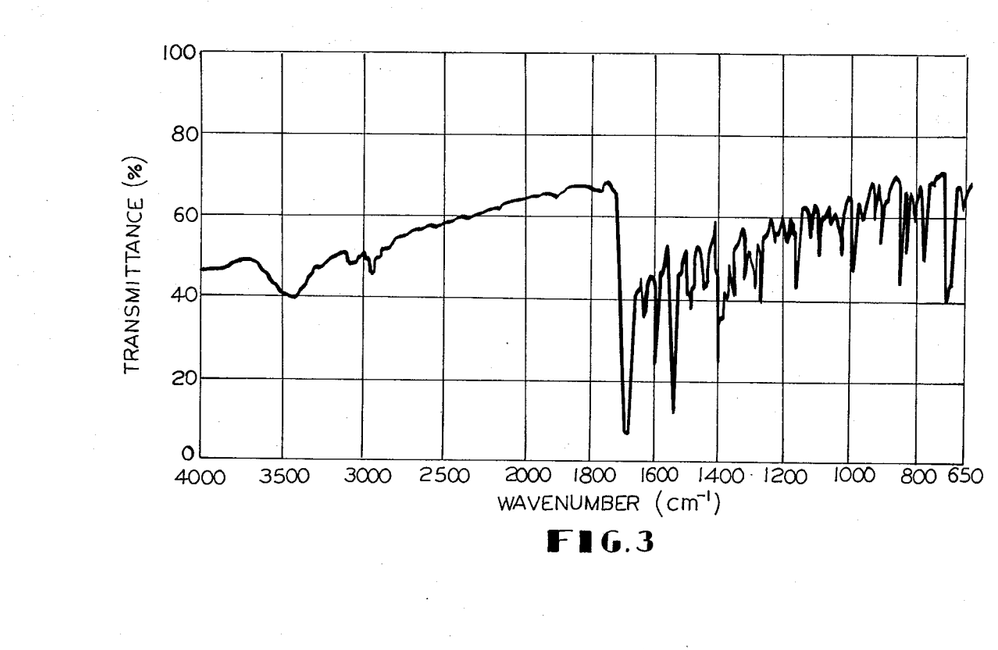

To a stirred suspension of 2.8 parts of 1-acetoacetyl-8-chloro-2-imino-6-phenyl-1,2,3,4-tetrahydro-1,5-benzodiazocine in 50 parts by volume of ethanol is added 10 parts by volume of ethanol saturated with hydrogen chloride under ice cooling. The reaction mixture is further stirred for 45 minutes at 0°–10°C. The resulting colorless crystals are collected by filtration and washed with acetone to give 10-chloro-5,6-dihydro-3-methyl-8-phenyl-1H-pyrimido(1,2-a)-(1,5)benzodiazocin-1-one hydrochloride. The crystals are partitioned between 20 parts by volume of chloroform and 10 parts by volume of 6% aqueous ammonia in water. The chloroform layer is separated, washed with water and, dried over sodium sulfate, then the solvent is removed under reduced pressure. The residue is purified by silica gel chromatography to give 10-chloro-5,6-dihydro-3-methyl-8-phenyl-1H-pyrimido(1,2-a)(1,5) benzodiazocin-1-one as colorless crystals. Recrystallization from dichloromethane-n-hexane gives colorless prisms. Melting point 184°–185°C.

Elementary analysis: $C_{20}H_{16}ClN_3O$. Calculated: C 68.67, H 4.61, N 12.01. Found: C 68.65, H 4.52, N 11.93.

The infrared absorption spectrum of the product is shown in FIG. 3.

The following compounds are prepared in a similar manner to that in Examples 3 and 4.

| Starting material | Product | Melting point (°C) |
|---|---|---|
| 1-acetoacetyl-2-imino-6-phenyl-1,2,3,4-tetrahydro-1,5-benzodiazocine | 5,6-dihydro-3-methyl-8-phenyl-1H-pyrimido(1,2-a)-(1,5)benzodiazocin-1-one | 169–170 |
| 1-acetoacetyl-2-imino-8-methyl-6-phenyl-1,2,3,4-tetrahydro-1,5-benzodiazocine | 5,6-dihydro-3,10-dimethyl-8-phenyl-1H-pyrimido-(1,2-a)(1,5)bezodiazocin-1-one | 150–152 |
| 1-acetoacetyl-8,9-dimethoxy-2-imino-6-phenyl-1,2,3,4-tetrahydro-1,5-benzodiazocine | 5,6-dihydro-10,11-dimethoxy-3-methyl-8-phenyl-1H-pyrimido-(1,2-a)(1,5)benzodiazocin-1-one | 195–196 |
| 1-acetoacetyl-8-chloro-2-imino-4-methyl-6-phenyl-1,2,3,4-tetrahydro-1,5-benzodiazocine | 10-chloro-5,6-dihydro-3,6-dimethyl-8-phenyl-1H-pyrimido(1,2-a)(1,5)-benzodiazocin-1-one | 191–193 |

EXAMPLE 5

A suspension of 0.5 part of 2-acetoacetamido-8-chloro3,4-dihydro-6-phenyl-1,5-benzodiazocine in 18 parts by volume of absolute toluene is heated at 110°C for 2 hours. The solvent is evaporated under reduced pressure. The residue is chromatographed on silica gel using chloroform-methanol-ethyl acetate (85:10:5) as eluent to give 10-chloro-5,6-dihydro-3methyl-8-phenyl-1H-pyrimido(1,2-a)(1,5)benzodiazocin1-one as colorless crystals. Melting point 180°–183°C.

The IR-spectrum of this compound is identical with that of the compound obtained in EXAMPLE 4.

The following compounds are prepared in a similar manner to that in Example 5.

| Starting material | Product | Reaction temperature (°C) Solvent | Melting point (°C) |
|---|---|---|---|
| 2-acetoacetamido-3,4-dihydro-6-phenyl-1,5-benzodiazocine | 5,6-dihydro-3-methyl-8-phenyl-1H-pyridimo-(1,2-a)(1,5)benzodiazocin-1-one | 113<br>toluene | 169–170 |
| 2-acetoacetamido-3,4-dihydro-8-methyl-6-phenyl-1,5-benzodiazocine | 5,6-dihydro-3,10-dimethyl-8-phenyl-1H-pyrimido(1,2-a)(1,5)-benzodiazocin-1-one | 113<br>toluene | 150–152 |
| 2-acetoacetamido-3,4-dihydro-8,9-dimethoxy-6-phenyl-1,5-benzodiazocine | 5,6-dihydro-10,11-dimethoxy-3-methyl-8-phenyl-1H-pyrimido-(1,2-a)(1,5)-benzodiazocin-1-one | 78<br>benzene | 195–196 |
| 2-acetoacetamido-8-chloro-3,4-dihydro-4-methyl-6-phenyl- | 10-chloro-5,6-dihydro-3,6-dimethyl-8-phenyl-1H-pyrimido(1,2-a)- | 137 | 191–193 |

| Starting material | Product | Reaction temperature (°C) Solvent | Melting point (°C) |
|---|---|---|---|
| 1,5-benzodiazocine | (1,5)benzodiazocin-1-one | xylene | |
| 2-acetoacetamido-8-chloro-6-(4-chlorophenyl)-3,4-dihydro-3-methyl-1,5-benzodiazocine | 10-chloro-8-(4-chlorophenyl)-5,6-dihydro-3,5-dimethyl-1H-pyrimido(1,2-a)-(1,5)benzodiazocin-1-one | 113 toluene | 214–215 |

EXAMPLE 6

A suspension of 0.735 part of 1-acetoacetyl-8-chloro-2-imino-6-phenyl-1,2,3,4-tetrahydro-1,5-benzodiazocine in 25 parts by volume of absolute toluene is heated at 110°C for 1.5 hour. The solvent is evaporated under reduced pressure. The residue is chromatographed on silica gel using chloroform-methanol-ethyl acetate (85:10:5) as eluent to give 10-chloro-5,6-dihydro-3-methyl-8-phenyl-1H-pyrimido(1,2-a)(1,5) benzodiazocin-1-one as colorless crystals. Melting point 181°–182°C.

The following compounds are prepared in a similar manner to that in Example 6.

| Starting material | Product | Reaction temperature (°C) Solvent | Melting point (°C) |
|---|---|---|---|
| 1-acetoacetyl-2-imino-6-phenyl-1,2,3,4-tetrahydro-1,5-benzodiazocine | 5,6-dihydro-3-methyl-8-phenyl-1H-pyrimido-(1,2-a)(1,5)-benzodiazocin-1-one | 113 toluene | 169–170 |
| 1-acetoacetyl-2-imino-8-methyl-6-phenyl-1,2,3,4-tetrahydro-1,5-benzodiazocine | 5,6-dihydro-3,10-dimethyl-8-phenyl-1H-pyrimido(1,2-a)(1,5)-benzodiazocin-1-one | 113 toluene | 150–152 |
| 1-acetoacetyl-8,9-dimethoxy-2-imino-6-phenyl-1,2,3,4-tetrahydro-1,5-benzodiazocine | 5,6-dihydro-10,11-dimethoxy-3-methyl-8-phenyl-1H-pyrimido-(1,2-a)(1,5)-benzodiazocin-1-one | 78 benzene | 195–196 |
| 1-acetoacetyl-8-chloro-2-imino-4-methyl-6-phenyl-1,2,3,4-tetrahydro-1,5-benzodiazocine | 10-chloro-5,6-dihydro-3,6-dimethyl-8-phenyl-1H-pyrimido(1,2-a)(1,5)-benzodiazocin-1-one | 137 xylene | 191–193 |
| 1-acetoacetyl-8-chloro-6-(4-chlorophenyl)-2-imino-3-methyl-1,2,3,4-tetrahydro-1,5-benzodiazocine | 10-chloro-8-(4-chlorophenyl)-5,6-dihydro-3,5-dimethyl-1H-pyrimido(1,2-a)(1,5)-benzodiazocin-1-one | 113 toluene | 214–215 |

What we claim is:

1. A compound of the formula wherein  stands for the partial structure wherein $R^1$ stands for hydrogen, alkyl having 1 to 6 carbon atoms, or phenyl, $R^2$ and $R^3$, respectively, stand for hydrogen or alkyl having 1 to 3 carbon atoms, and each of rings A and B are unsubstituted or substituted by up to two substituents, which may be the same or different, said substituents being halogen, nitro, trifluoromethyl, alkyl having 1 to 4 carbon atoms, or alkoxy having 1 to 4 carbon atoms, or a pharmaceutically acceptable acid addition salt thereof.

2. The compound as claimed in claim 1, wherein $R^1$ is hydrogen.

3. The compound as claimed in claim 1, wherein rings A and B are unsubstituted or substituted by up to two substituents selected from halogen, alkyl of 1 to 4 carbon atoms, or an alkoxy having 1 to 4 carbon atoms.

4. The compound as claimed in claim 1, namely 10-chloro-5,6-dihydro-3-methyl-8-phenyl-1H-pyrimido(1,2-a)(1,5)benzodiazocin-1-one.

5. The compound as claimed in claim 1, namely 5,6-dihydro-3-methyl-8-phenyl-1H-pyrimido(1,2-a)(1,5)benzodiazocin-1-one.

6. The compound as claimed in claim 1, namely 5,6-dihydro-3,10-dimethyl-8-phenyl-1H-pyrimido(1,2-a)(1,5)benzodiazocin-1-one.

7. The compound as claimed in claim 1, namely 5,6-dihydro-10,11-dimethoxy-3-methyl-8-phenyl-1H-pyrimido(1,2-a)(1,5)benzodiazocin-1-one.

8. The compound as claimed in claim 1, namely 10-chloro-5,6-dihydro-3,6-dimethyl-8-phenyl-1H-pyrimido(1,2-a)(1,5)benzodiazocin-1-one.

9. The compound as claimed in claim 1, namely 10-chloro-8-(4-chlorophenyl)-5,6-dihydro-3,5-dimethyl-1H-pyrimido-(1,2-a)(1,5)benzodiazocin-1-one.

10. The compound as claimed in claim 1, namely 10-chloro-5,6-dihydro-1-methyl-8-phenyl-3H-pyrimido(1,2-a)(1,5)benzodiazocin-3-one.

11. The compound as claimed in claim 1, namely 5,6-dihydro-1-methyl-8-phenyl-3H-pyrimido(1,2-a)(1,5)benzodiazocin-3-one.

12. The compound as claimed in claim 1, namely 5,6-dihydro-1,10-dimethyl-8-phenyl-3H-pyrimido(1,2-a)(1,5)benzodiazocin-3-one.

13. The compound as claimed in claim 1, namely 5,6-dihydro-10,11-dimethoxy-1-methyl-8-phenyl-3H-pyrimido(1,2-a)(1,5)benzodiazocin-3-one.

14. The compound as claimed in claim 1, namely 10-chloro-5,6-dihydro-1,6-dimethyl-8-phenyl-3H-pyrimido(1,2-a)(1,5)benzodiazocin-3-one.

15. The compound as claimed in claim 1, namely 10-chloro-8-(4-chlorophenyl)-5,6-dihydro-1,5-dimethyl-3H-pyrimido-(1,2-a)(1,5)benzodiazocin-3-one.

* * * * *